United States Patent [19]
Khaiat

[11] Patent Number: 5,741,496
[45] Date of Patent: Apr. 21, 1998

[54] PROCESS FOR THE TREATMENT OF SKINS HAVING DRY AREAS AND GREASY AREAS

[75] Inventor: Alain Khaiat, Paris, France

[73] Assignee: Laboratoires De Biologie Vegetale Yves Rocher, La Gacilly, France

[21] Appl. No.: 593,480

[22] Filed: Jan. 29, 1996

Related U.S. Application Data

[63] Continuation of Ser. No. 305,929, Sep. 19, 1994, abandoned.

[30] Foreign Application Priority Data

Sep. 21, 1993 [FR] France ................. 93 11240

[51] Int. Cl.$^6$ ............... A61K 7/00; A61K 7/48
[52] U.S. Cl. ............ 424/401; 424/195.1; 514/847; 514/848
[58] Field of Search ............ 424/401, 195.1; 514/847, 848

[56] References Cited

U.S. PATENT DOCUMENTS

| | | | |
|---|---|---|---|
| 4,386,067 | 5/1983 | Guillon | 424/95 |
| 4,946,832 | 8/1990 | Goode et al. | 514/53 |
| 5,219,558 | 6/1993 | Woodin et al. | 424/59 |
| 5,256,649 | 10/1993 | Le Fur et al. | 514/46 |
| 5,510,100 | 4/1996 | Picard et al. | 424/59 |

FOREIGN PATENT DOCUMENTS

| | | |
|---|---|---|
| 0 039 857 | 11/1981 | European Pat. Off. . |
| 0 117 613 | 9/1984 | European Pat. Off. . |
| 0 183 322 | 6/1986 | European Pat. Off. . |
| 0 281 812 | 9/1988 | European Pat. Off. . |
| 0 388 275 | 9/1990 | European Pat. Off. . |
| 0 414 605 | 2/1991 | European Pat. Off. . |
| 2 287 214 | 5/1976 | France . |
| 2 305 172 | 10/1976 | France . |
| 2 405 068 | 5/1979 | France . |
| 2 648 347 | 12/1990 | France . |
| 2 692 480 | 12/1993 | France . |
| 57-23793 | 11/1983 | Japan . |
| 60-296284 | 12/1987 | Japan . |
| 1-193207 | 8/1989 | Japan . |

OTHER PUBLICATIONS

"Exotic Touches", *Soap, Perfumery & Cosmetics*, vol. 23n No. 12, Dec. 1990, London, Great Britain, p. 45.

*Primary Examiner*—Sally Gardner-Lane
*Attorney, Agent, or Firm*—Young & Thompson

[57] ABSTRACT

Process for the aesthetic treatment of persons who exhibit a dual character between two parts of their skin comprising a greasy area and a dry area, which comprises the application to the skin of a such person a cosmetic composition comprising an effective quantity of an emollient substance which also exhibits a lipase-inhibiting activity. The substance is selected from the group consisting of *Limnanthes alba* oil, *Jessenia bataua* oil, the unsaponifiable fraction of soya bean oil and shea butter. The effective quantity is, by weight percent of the entire composition:

| | |
|---|---|
| *Limnanthes alba* oil | 0.5 to 15% |
| *Jessenia bataua* oil | 0.5 to 15% |
| the unsaponifiable fraction of soya bean oil | |
| shea butter | to 10%. |

8 Claims, 3 Drawing Sheets

PROCESS FOR THE TREATMENT OF SKINS HAVING DRY AREAS AND GREASY AREAS

This application is a continuation of application Ser. No. 08/305,929, filed Sep. 19, 1994, now abandoned.

FIELD OF THE INVENTION

The present invention relates to the use, for the aesthetic treatment of skins having dry areas and greasy areas of an effective quantity of active substances.

BACKGROUND OF THE INVENTION

In cosmetology, such skins are the skins of persons who exhibit a dual character between two parts of their face, that is to say who have a greasy area and a dry area.

This dual character is essentially due to the distribution of the sebaceous glands. Thus, the greasy area represented by the forehead, the nose and the chin comprises 900 sebaceous glands per $cm^2$. The dry area represented by the cheeks comprises only 400 sebaceous glands per $cm^2$.

The difficulty for the cosmetologist lies in the development of products which should suit this combination of dry and greasy parts of the skin, while improving its general appearance.

The latest products known for the care of such skins is the product BIOPUR® from Biotherm and the product MOD-ERACTIVE® from Jeanne Gatineau. The principal activity of these products is to absorb the excess sebum and therefore to treat more particularly the greasy areas. The problem connected with mixed skins has therefore not been solved by the products mentioned.

It is known that the skin lipids of the skin surface represent a mixture of lipids synthesized by two sources: the sebaceous glands and the epidermis.

The role of these lipids has gone from simple plasticizing agent to that of epidermal barrier governing the water-retaining and receiving properties, the differences in permeability of agents applied locally, as well as the cohesion and the desquamation of the stratum corneum.

3% of the surface lipids are obtained from the secretion of the epidermis, whereas 97% are due to the excretion by the sebaceous glands.

Moreover, the circadian rhythm, the age and the sex of the person influence the level of excretion of lipids by the sebaceous glands.

Thus, between 13 and 20 years, the level of excretion by the sebaceous glands triples and then gradually decreases.

The sebaceous glands of a person of female sex having a normal skin secrete 0.75 to 1 $\mu g/cm^2/min$ of sebum whereas those of a person with mixed skin secrete in the greasy areas 50% sebum in addition to the normal level and they have a substantially decreased secretion in the dry areas.

Likewise, for persons of male sex, the level of secretion of a normal skin is 1 to 1.5 $\mu g/cm^2/min$, the level of secretion for mixed skins being in the greasy areas increased by 65%, and substantially decreased in the dry areas.

It is a fact that sebum, a fluid excreted by the sebaceous glands, is the principal source of surface skin lipids.

Now, sebum comprises 31% triglycerides, 5% diglycerides, 24% free fatty acids, 15% squalene and 25% waxes.

Thus, two facts prove to be characteristic of skins with dry and greasy areas.

For the dry areas, the substantial reduction in triglycerides, which may extend to disappearance in the most severe cases of xerosis.

For the greasy areas, the quantitative importance of triglycerides. These unfortunately do not remain at the "native" state, but are gradually degraded, under the action of enzymes, into diglycerides and monoglycerides, and finally into free fatty acids which are responsible for most mixed skin disorders and defects (shiny and greasy appearance, most often irritated surface, skin subject to an inflammatory response).

These enzymes, called lipases, are derived mainly from the skin flora: propionibacterium acnes, staphylococcus epidermidis, propionibacterium granulosum.

In the absence of being able to limit the production of sebum and therefore to act on the hormonal mechanisms, the authors of the present invention have sought to solve the problem of such skins by acting both on the greasy and dry regions.

SUMMARY OF THE INVENTION

The subject of the present invention is therefore the use, for the aesthetic treatment of such skins, of an effective quantity of one and the same substance having both emollient and lipase-inhibiting properties, or alternatively of the combination of an effective quantity of an emollient substance having no activity on the action of lipases and of a non-emollient substance exhibiting lipase-inhibiting activity.

The term "emollient" means that the substance has a beneficial activity for reestablishing the surface lipid coat and allowing the epidermis to retain its full suppleness and elasticity, as well as for contributing towards reestablishing the hydrolipid film.

The emollient substances are generally fatty acid esters such as fatty acid triglycerides, fatty alcohols or esters of fatty acids and fatty alcohol.

Among the emollient substances having a lipase-inhibiting activity, there may be mentioned *Limnanthes alba* (or Shambrila) oil, *Jessenia bataua* (or Hunguraghua) oil, the unsaponifiable fraction of soya bean oil and shea butter. Other substances not mentioned may obviously have the same activity.

Among the emollient substances having no activity on the action of lipases, there may be mentioned olive oil, isopropyl myristate, sweet almond oils, and hexyl ethyl cocoate. Generally, oils of plant origin can be used.

Among the non-emollient substances exhibiting an anti-lipase activity, there may be mentioned soya bean protein hydrolysate, wheat protein hydrolysate, copper or zinc acetate. Likewise, other substances not mentioned can be used. All these substances are well known to persons skilled in the art and can be easily obtained on the market in purified forms.

Substances with a double activity and substances with a single activity combined in the same composition, such as those previously mentioned, were tested. Shambrila oil proved particularly effective for the treatment of such skins. In cosmetics, refined Shambrila oil is particularly sought after for its silky feel, its emollient and moisturizing effect. It is extracted from the seeds of *Limnanthes alba*, whose unique characteristic is the fact that it consists at maturity of a very high level of triglycerides made up of very long-chain fatty acids ($C_{20}$–$C_{22}$). The oil contains 96% long-chain fatty acids of more than 20 carbons, of which 18% polyunsaturated fatty acids.

The method used to evaluate the required quantity of lipase-inhibiting substances to be used in the cosmetic compositions depends on the use of a simple apparatus. The pH and the temperature of an olive oil-water mixture are kept constant and an enzyme having properties comparable to the lipases of the skin flora is added thereto and placed in a water bath.

DETAILED DESCRIPTION OF THE INVENTION

Figure 1:
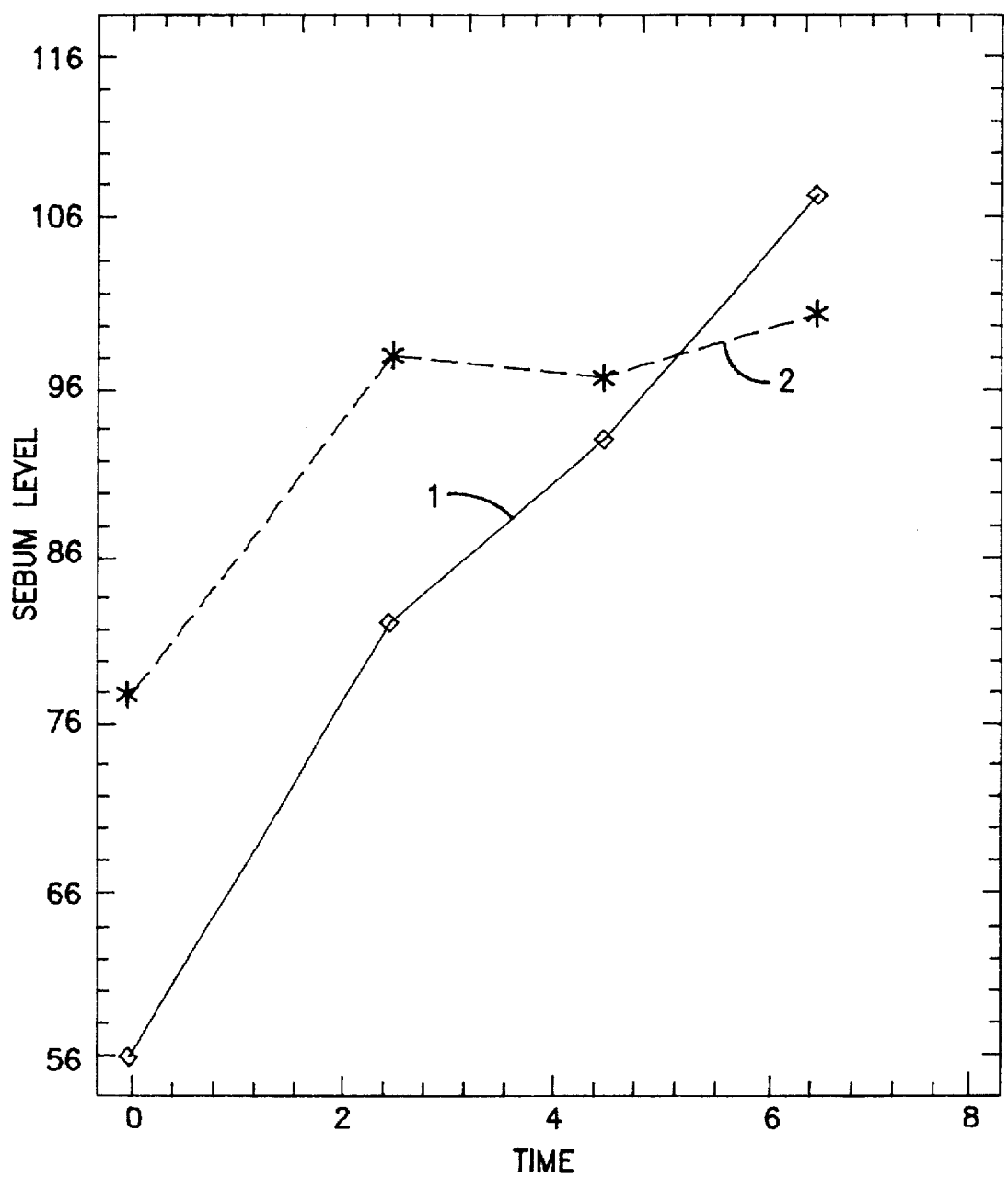
FIG. 1 is a graph of sebum level on the cheeks of a person having a mixed skin.

Thus, the mixture which constitutes the substrate is prepared by mixing 12 ml of olive oil, 15 ml of sodium azide (0.1% aqueous), 7.5 ml distilled water, 3 ml of test substance and 3 ml of TRIS buffer to obtain a pH of 8. 3 ml of a 5% aqueous solution of Rhizopus arrihzus lipase are then added.

Curves which make it possible to compare the antilipase substances with each other and to evaluate their activity as a function of their concentration in the reaction medium are then plotted.

The active substances having the lipase-inhibiting properties act via phenomena of stearic hindrance by plotting the active site of the enzyme.

The effective concentrations of the antilipase substances in the compositions of the present invention were therefore determined:

| | |
|---|---|
| Limnanthes alba oil | 0.5 to 15% |
| Jessenia bataua oil | 0.5 to 15% |
| shea butter | 1 to 10% |
| the unsaponifiable fraction of soya bean oil | 0.2 to 5% |
| Soya bean protein hydrolysate | 0.2 to 6% |
| Wheat protein hydrolysate | 0.2 to 6% |
| Copper acetate | 0.002 to 0.01% |

Tests were then carried out by measuring the sebum level on the skin before and after applying for two weeks the product(s) identified as being active as lipase inhibitor and emollient. Cleansing emulsions and lotions and creams were tested as a function of the percentage by weight of the active substances. In these trials, the following compositions were used as composition according to the invention:

| Cleansing emulsion: | | |
|---|---|---|
| Glycerin | | 5.0% |
| Polyacrylamide gel | | 2.0% |
| Limnanthes oil | | 1.0% |
| Ethyl hexyl cocoate | | 1.0% |
| cyclomethicone | | 2.0% |
| hydrogenated castor oil (40 EO) | | 1.0% |
| Perfume | | 0.2% |
| Preservatives | | 0.6% |
| Water | qs | 100 |
| Lotion: | | |
| Glycerin | | 5.0% |
| Polyacrylamide gel | | 1.7% |
| Cyclomethicone | | 2.0% |

| -continued | | |
|---|---|---|
| Limnanthes oil | | 0.5% |
| Mineral oil | | 2.5% |
| Perfume | | 0.3% |
| Preservatives | | 0.5% |
| Water | qs | 100 |
| Cream: | | |
| Stearic acid (40 EO) | | 2.5% |
| Ethyl hexyl palmitate | | 4.0% |
| Propylene glycol dioctanoate | | 4.0% |
| Stearyl alcohol | | 2.5% |
| Limnanthes oil | | 3.0% |
| Glycol dibehenate | | 3.0% |
| Cyclomethicone | | 3.0% |
| Polymethiconol | | 2.0% |
| Hydrogenated soya bean oil | | 3.5% |
| Preservatives | | 0.5% |
| Water | qs | 100 |
| Glycerin | | 5.0% |
| Polyacrylamide gel | | 3.0% |
| Perfume | | 0.3% |

In each figure, curve 1 corresponds to the application of a reference composition not containing the active substance (s) of the invention. Likewise, curve 2 corresponds to the successive application of a cleansing emulsion, a lotion and a cream daily for two weeks (including the day the measurement is carried out).

Figure 2:
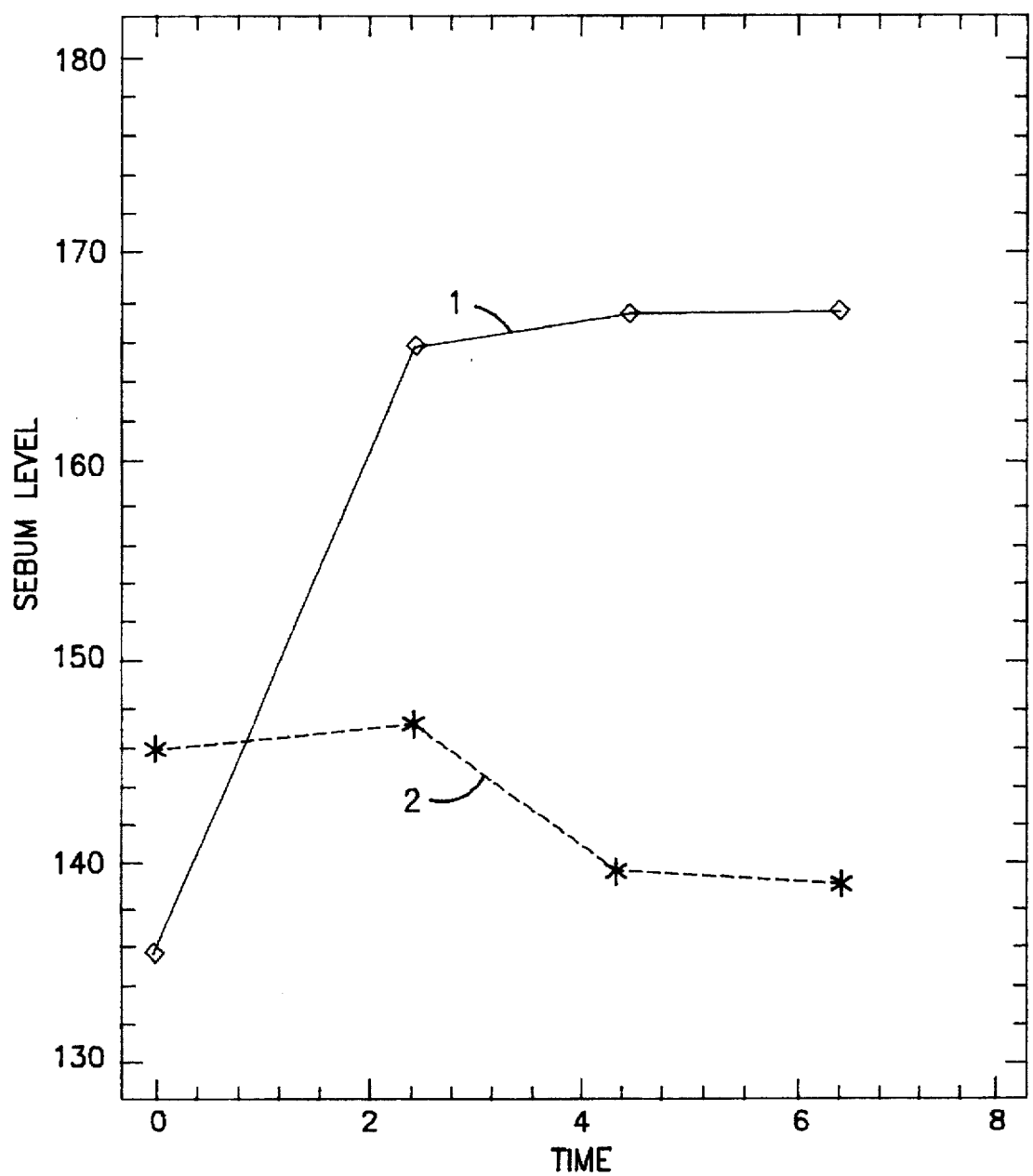
FIG. 2 is a graph of sebum level versus time on the nose of a person having a mixed skin.
Figure 3:
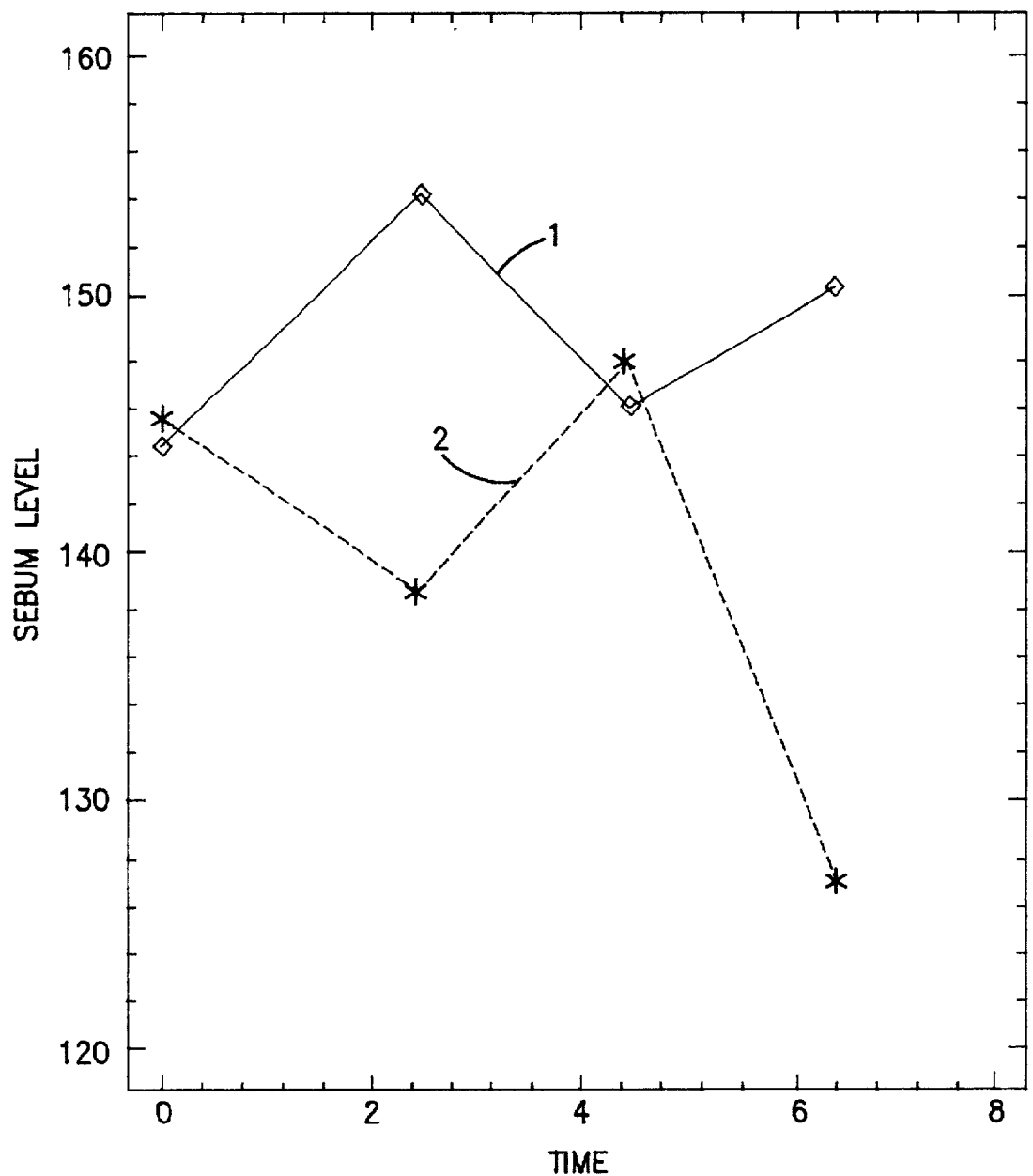
FIG. 3 is a graph of sebum level versus time on the chin of a person having a mixed skin.

Results of FIGS. 1, 2 and 3

Fig. 1 shows that when the composition of the present invention is applied on the cheeks, the sebum level is initially higher, then increases further and becomes stabilized at a level which is adequate for an emollient activity to be exerted on the dry part of the skin. In contrast, the other trial shows a sebum level which is very low initially and very high after 6 hours.

FIG. 2 shows that when the composition of the present invention is applied to the nose, the sebum level becomes stabilized within a low range. The other reference trial shows a sebum level which increases very substantially.

FIG. 3 shows that when the composition of the present invention is applied to the chin, the sebum level decreases substantially after more than 4 hours. In contrast, the reference trial shows that the sebum level, after 4 hours, tends to increase.

Thus, the results indicate with the composition according to the invention a clear increase in sebum in the dry parts (cheeks), and a clear decrease in sebum in the greasy parts (nose, chin).

In addition to the antilipase activity on the greasy areas, the cosmetic compositions of the present invention therefore have an emollient activity on the dry areas.

The embodiment of the cream is illustrated below. The oily phase is heated to 80°/85° C., with stirring, the aqueous phase is heated separately to 80°/85° C., with stirring. The oily phase is then added to the aqueous phase, with vigorous stirring. The mixture is then allowed to cool while stirring slowly. When the mixture reaches a temperature close to 30° C., the perfume is added.

The examples of formulations below are not limiting. The quantities of effective active substances depend on the types of formulation and the various constituents chosen, knowing that the effectiveness of the treatment lies in the two types of antilipase activities and emollient effect, the effective quantities being determined so that the composition does not exhibit too greasy an appearance, is not irritating either and of course is effective for the treatment of mixed skins.

| Protective cream: | | |
|---|---|---|
| Limnanthes oil | | 12% |
| Cetyl alcohol | | 2.0% |
| UVB-screening agent | | 2.0% |
| UVA-screening agent | | 1.2% |
| Polyoxyethylenated lauryl alcohol | | 2.5% |
| Sorbitan stearate | | 2.5% |
| Polyoxyethylenated sorbitan stearate | | 1.0% |
| Tetrasodium EDTA | | 0.1% |
| Carbopol | | 0.35% |
| Sodium hydroxide | | 0.10% |
| Perfume | | 0.2% |
| Preservatives | | 0.4% |
| Water | qs | 100 |

| Serum: | | |
|---|---|---|
| Olive oil | | 9.0% |
| Ethyl hexyl cocoate | | 9.0% |
| Tocopherol acetate | | 0.05% |
| Cyclomethicone | | 1.5% |
| Sucrose stearate | | 4.0% |
| Sucrose distearate | | 1.5% |
| Hydrogenated castor oil (40 EO) | | 0.8% |
| Xanthan gum | | 0.2% |
| Preservatives | | 0.5% |
| Urea | | 3.0% |
| Perfume | | 0.3% |
| Hydrolysed wheat proteins | | 6% |
| Water | qs | 100 |

| Lotion: | | |
|---|---|---|
| Sweet almond oils | | 7.5% |
| Cyclomethicone | | 4.0% |
| Dimethicone | | 5.0% |
| Butylene glycol | | 6.0% |
| Copper acetate | | 0.004% |
| Preservatives | | 0.4% |
| Perfume | | 0.3% |
| Water | qs | 100 |

| Treatment cream | | |
|---|---|---|
| Polyisobutene 6-8 | | 5.0% |
| Microcrystalline wax | | 1.5% |
| Glycerol stearate | | 3.0% |
| Sorbitan palmitate (20 EO) | | 1.0% |
| Shea butter | | 6.0% |
| Soya bean unsaponifiable matter | | 6.0% |
| BHA | | 0.05% |
| Preservatives | | 0.5% |
| Propylene glycol | | 3.0% |

-continued

| | | |
|---|---|---|
| Perfume | | 0.4% |
| Water | qs | 100 |

I claim:

1. Process for inhibiting the lipase activity on the skin in greasy areas while reestablishing the lipid coat of the dry areas of a person exhibiting a skin having both greasy and dry areas, comprising applying to a said skin an effective quantity of a substance selected from the group consisting of *Limnanthes alba* oil, and *Jessenia bataua* oil, said effective quantity being, by weight of the entire composition:

| | |
|---|---|
| *Limnanthes alba* oil | 0.5 to 15% |
| *Jessenia bataua* oil | 0.5 to 15%. |

2. Process as claimed in claim 1, in which the substance is *Limnanthes alba* oil.

3. Process as claimed in claim 1, in which the substance is *Jessenia bataua* oil.

4. Process as claimed in claim 1, in which the composition is in the form of a cream, a serum or a lotion.

5. Process for decreasing the lipid level in greasy areas while increasing the sebum level in the dry areas of a person exhibiting a skin having both greasy areas and dry areas, comprising applying to a said skin a cosmetic composition comprising an effective quantity of a substance selected from the group consisting of *Limnanthes alba* oil, and *Jessenia bataua* oil, said effective quantity being, by weight of the entire composition:

| | |
|---|---|
| *Limnanthes alba* oil | 0.5 to 15% |
| *Jessenia bataua* oil | 0.5 to 15%. |

6. Process as claimed in claim 5, in which the substance is *Limnanthes alba* oil.

7. Process as claimed in claim 5, in which the substance is *Jessenia bataua* oil.

8. Process as claimed in claim 5, in which the composition is in the form of a cream, a serum or a lotion.

* * * * *